United States Patent [19]

Singer et al.

[11] Patent Number: 5,267,946
[45] Date of Patent: Dec. 7, 1993

[54] KNEE BRACE WITH ADJUSTABLE RIGID POSTERIOR STRUT

[76] Inventors: Samuel Singer, 125 Timbersprings La.; Jeffrey A. Fried, 499 S. Ben Franklin Rd., both of, Indiana, Pa. 15701

[21] Appl. No.: 861,722

[22] Filed: Apr. 1, 1992

[51] Int. Cl.$^5$ .............................................. A61F 5/00
[52] U.S. Cl. ........................................ 602/16; 602/26
[58] Field of Search .......................... 602/5, 16, 23–26; 606/74; 16/110 R; 24/298

[56] References Cited

U.S. PATENT DOCUMENTS

| 2,144,641 | 1/1939 | Snyder . | |
|---|---|---|---|
| 2,179,903 | 11/1939 | Spears . | |
| 3,026,869 | 3/1962 | Peach . | |
| 3,093,131 | 6/1963 | Kashyap | 602/23 |
| 3,194,233 | 7/1965 | Peckham . | |
| 3,419,002 | 12/1968 | Santosus | 602/23 |
| 3,669,105 | 6/1972 | Castiglia . | |
| 3,712,299 | 1/1973 | Voehl . | |
| 3,931,817 | 1/1976 | Infranca | 602/24 |
| 4,191,373 | 3/1980 | Lancellotti | 602/16 X |
| 4,372,298 | 2/1983 | Lerman . | |
| 4,572,170 | 2/1986 | Cronk et al. . | |
| 4,946,156 | 8/1990 | Hart | 602/23 X |
| 5,133,341 | 7/1992 | Singer et al. | 602/26 X |

FOREIGN PATENT DOCUMENTS 2215213  9/1989 United Kingdom .

Primary Examiner—Richard J. Apley
Assistant Examiner—Linda C. M. Dvorak
Attorney, Agent, or Firm—Richard V. Westerhoff

[57] ABSTRACT

A knee brace has an adjustable rigid posterior strut with an arcuate member which extends through the popliteal space behind the knee joint and is made of two halves which can be extended or retracted axially or rotated with respect to one another. Terminal portions of the strut, to which supports secured to the leg and thigh are hinged, are adjustably secured by ball and socket connections to mounting members which in turn are adjustably attached to the arcuate member by stems which telescope into and rotate within bores in the ends of the two halves of the arcuate member. With these adjustments the components of the posterior strut can be locked in a myriad of configurations to accommodate for various sizes and deformities of protected joints.

27 Claims, 3 Drawing Sheets

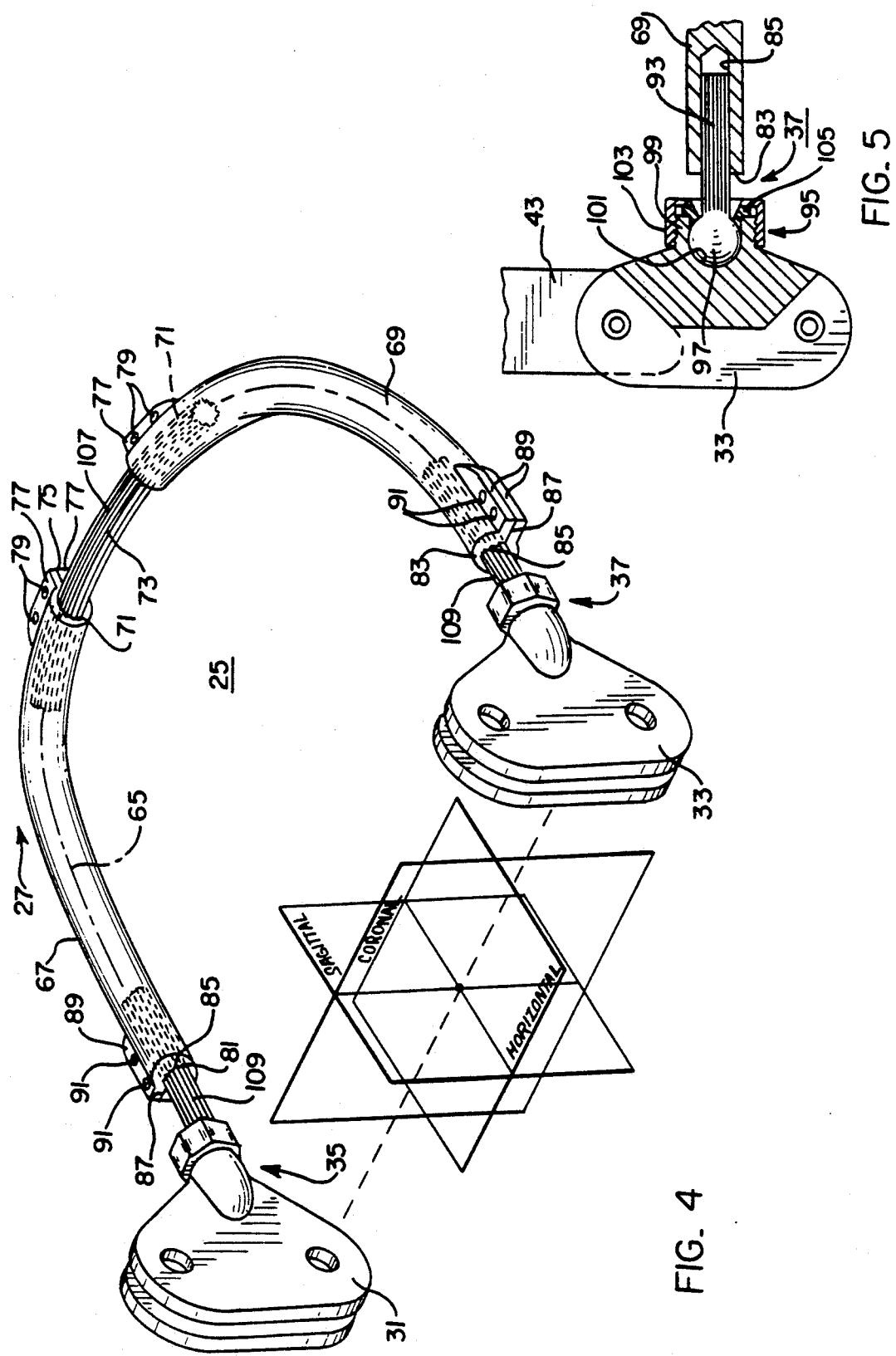

KNEE BRACE WITH ADJUSTABLE RIGID POSTERIOR STRUT

BACKGROUND OF INVENTION

1. Field of Invention

This invention relates to a knee brace with a posterior strut and generally triangular stiff cuff members which transmit forces around the knee joint, and more particularly to such a knee brace in which the rigid posterior strut is adjustable in several degrees of freedom to accommodate for a wide range of abnormalities in, and sizes of, the protected joint.

2. Background Information

Our copending application Ser. No. 07/662,879 filed on Mar. 1, 1991 now U.S. Pat. No. 5,133,341 and entitled "Knee Brace with Posterior Strut" discloses a unique knee brace having a rigid posterior strut with an arcuate section extending through the popliteal space behind the knee joint and terminal portions positioned on either side of, but spaced from, the joint. A superior elongated support member is pivotally connected to one terminal portion of the strut and extends upward along one side, preferably the medial side, of the thigh, and is secured to the fleshy part of the thigh by cushioned straps. An inferior elongated support member is pivotally connected to the other terminal portion of the strut and extends downward along the opposite side, preferably the lateral side, of the leg and is secured to the fleshy part of the leg by additional cushioned straps.

The posterior strut of this brace performs several functions. First, it is the basic element to which the other components of the brace are attached. Second, it transmits forces applied to the lateral side of the knee around the joint to the medial side and into the fleshy part of the thigh through the hinged support. Similarly, medially applied forces are transmitted around the knee joint by the posterior strut to the lateral side where they are dissipated in the fleshy part of the leg.

A third and very important function of the posterior strut is the repositioning of the hinge points for the support members on the terminal portions of the strut to accommodate for femoral rollback during flexion of the joint. This repositioning is effected by rotation of the arcuate portion of the strut which is clamped between the fleshy portions of the backs of the thigh and the calf. This construction eliminates the need for the very complex compound hinge mechanisms found in many knee braces.

The knee brace of our copending application also preferably includes a pair of stiff, bowed anterior cuffs. These cuffs are generally triangular in shape with one edge secured to one of the elongated supports and the opposite vertex pivotally connected to the opposite terminal portion of the strut. These stiff cuffs, together with the posterior strut, transmit torsion forces around the knee joint without interfering with normal flexion of the joint. As an elongated support need only be attached to one side of the thigh and the other side of the leg, the unique Z configuration of our knee brace makes it easier to fit the brace to the wearer, while providing superior protection. In an alternative, functional (special application) form of the brace, elongated support members hinged to both the terminal portions of the posterior strut extend upward and downward and are attached to the lateral and medial sides of both the thigh and the leg. Pairs of criss-crossing, stiff, anterior cuffs are secured to each of the elongated support members and are pivotally connected to the opposite terminal portion of the posterior strut.

While the knee brace of our copending application provides very good support for an injured, diseased or malformed knee joint, there is a need for a knee brace with a posterior strut which can be readily and easily adjusted to accommodate for individual knee characteristics and provide the surgeon/physiotherapist with a means for adjusting for abnormal knees for either improved brace fit, optimizing brace function/action for individual patients, or compensating for or controlling specific motions or actions. Adjustments may also be required or desirable during the course of treatment to accommodate for reduction in swelling, changes caused by treatment, or growth as in a child. It would also be desirable to have a single, or only a few basic sizes of the brace, which could be readily adapted to the circumstances, as opposed to the custom modeling and fabrication or the stocking of numerous sizes as required by many other braces.

SUMMARY OF THE INVENTION

These and other needs are satisfied by the invention which is directed to a posterior strut, and a knee brace incorporating the posterior strut, which is adjustable in many degrees of freedom to accommodate for individual joint characteristics and abnormalities, and changes thereof, and to reduce the number of sizes of the brace which must be stocked.

More particularly, the terminal members of the strut are connected to the arcuate center member by mounting means adjustably fixing the terminal members to the ends of the arcuate member in selected positions. Such adjustments include axial and rotational positioning of the terminal members relative to the longitudinal axis of the arcuate member. They may further include rotational adjustment of the terminal members about lateral and vertical axis transverse to the longitudinal axis of the arcuate member. Preferably, the mounting means includes mounting members having elongated members which telescope within bores in the ends of the arcuate member and which are secured in the selected axial and rotational positions by clamps which may be formed by confronting flanges on each side of slits along the bores in the ends of the arcuate member and screws which draw the flanges together.

The mounting means also includes attachment means fixing the terminal members to the mounting members in selectable positions. Preferably, the attachment means is a ball and socket connection. With this arrangement, the terminal members may be fixed in any angular position desired relative to the arcuate member and the anterior/posterior size of the strut can be adjusted.

Also preferably, the arcuate member comprises two halves joined by an elongated piece which telescopes into the two halves. The two halves may be extended axially along the elongated piece to adjust the lateral/medial dimension of the strut, and rotated about the elongated piece to adjust their relative angular positions in the sagittal (anterior-posterior) plane. The two halves of the arcuate member are clamped to the stem in the selected axial and angular positions by clamps similar to those which secure the terminal member mounts to the ends of the arcuate member. Preferably, the elongated members of the mounts and the elongated piece joining the two halves of the arcuate member, as well as the bores in the arcuate member are fluted to more securely fix the parts in the selected positions.

The knee brace incorporating the strut has generally triangular, stiff cuffs secured along one edge to one of the support members hinged to the terminal members and extending either upward along the thigh or downward along the leg. The opposite vertex is pivotably connected to the terminal member on the opposite side. These cuffs are anterior to the thigh and leg and are bowed so that they can accommodate for small adjustments of the terminal members. For larger adjustments, the cuffs are attached to the elongated member by a pivot member and fastening means spaced from the pivot member which accommodates for rotation of the cuff about the pivot member to a selected angular position and fixedly secures the cuff to the elongated support member at the selected angular position. Preferably, the fastening means are slots in the cuffs and fasteners extending through the slots and clamping the cuffs in the selected positions.

BRIEF DESCRIPTION OF THE DRAWINGS

A full understanding of the invention can be gained from the following description of the preferred embodiments when read in conjunction with the accompanying drawings in which:

FIG. 4 is an isometric view in enlarged scale of a posterior strut which forms a part of the knee brace of FIGS. 1 and 2.

FIG. 5 is a fragmentary view, partially in section, of one end of the posterior strut shown in FIG. 4.

DESCRIPTION OF THE PREFERRED EMBODIMENTS

Figures 1, 2:
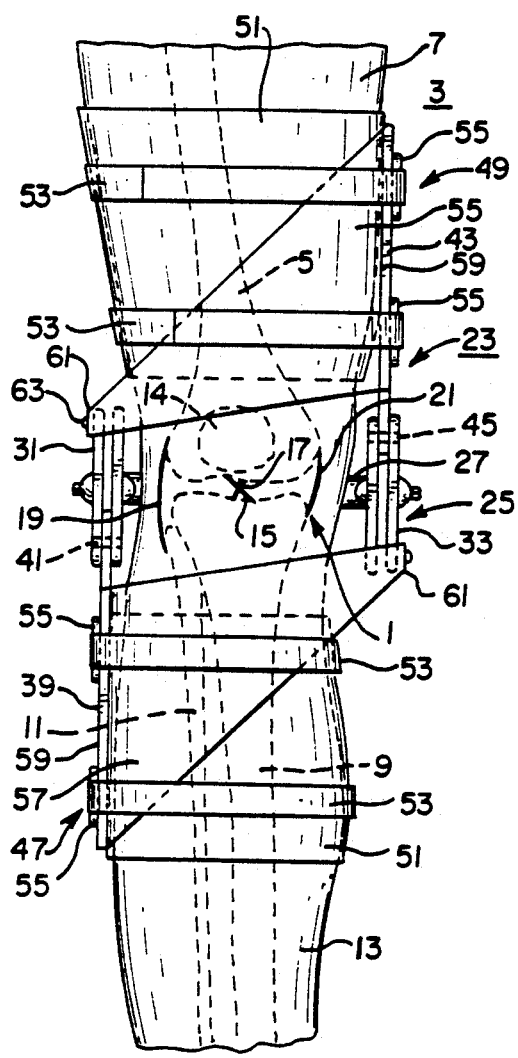
FIG. 1 is a front elevation view of a knee brace in accordance with the invention shown in use protecting a right knee joint shown in extension.
FIG. 2 is a side elevation view of the knee brace of FIG. 1.

FIG. 1 illustrates a knee brace in accordance with the invention in use in supporting and stabilizing a knee joint 1 of a human right lower extremity 3. The knee joint 1 is formed by the enlarged ends of the femur 5, which is the bone of the thigh 7, and the upper end of the tibia 9 which together with the fibula 11 form the bones of the leg 13. The patella (knee cap) 14 articulates with the distal end of the femur 5.

The joint 1 is held together by an arrangement of ligaments including the anterior cruciate ligament 15, the posterior cruciate ligament 17, the lateral collateral ligament 19 and the medial collateral ligament 21. Shear forces and torsional forces applied to the knee joint can result in stretching, and even tearing of these ligaments. A common injury occurs when a lateral blow is applied to the outside of the thigh with the foot planted. This causes the knee joint to buckle inward resulting in tearing of the medial collateral ligament 21, and occasionally the anterior cruciate ligament 15 as well.

The knee brace of the present invention is an improvement upon the knee brace described in our copending U.S. application Ser. No. 07/662,879 filed on Mar. 1, 1991 which is hereby incorporated by reference. The improved knee brace of the present invention provides several degrees of freedom in adjustment of the knee brace of the copending application.

The improved knee brace 23 shown in FIGS. 1 and 2 includes an adjustable rigid posterior strut 25. The strut 25 comprises an arcuate member 27 which extends behind the knee joint 1 through the popliteal area 29 (see FIG. 2). Terminal members 31 and 33 are secured to the arcuate member 27 by mounting members 35 and 37 respectively. The terminal members 31 and 33 are adjacent, but spaced from the lateral and medial sides, respectively of the knee joint 1.

An inferior lateral rigid elongated support member 39 is pivotally connected to the lateral terminal member 31 of the rigid posterior strut 25 at a first pivot point by a pivot pin 41 and extends down along the lateral side of the leg 13. A superior medial rigid elongated support member 43 is pivotally connected to the terminal member 33 of the adjustable rigid posterior strut 25 at a second pivot point by pivot pin 45, and extends upward medially along the thigh 7.

The support members 39 and 43 are secured to the leg 13 and thigh 7 respectfully by anchoring devices 47 and 49. The anchoring devices 47 and 49 each include a sleeve 51 of a non-slip cushioning material, such as, for instance, neoprene, and a pair of straps 53 which are threaded through buckles 55 on the support members 39 and 43 and secured such as by VELCRO fasteners (not shown). These anchoring devices 47 and 49 permanently secure the support members 39 and 43 to the fleshy portions of the leg 13 and the thigh 7, respectively, so that forces are transmitted through these support members into the large muscles of the extremity 3.

The brace 23 is also provided with a pair of stiff, semi-rigid, anterior cuff members 57. These cuff members are generally triangular in shape with one edge 59 secured to the associated elongated support member 39 or 43 and with the opposing vertex 61 pivotally connected, such as with a snap fastener 63, to a connection point on the terminal member 31 or 33 opposite to the terminal member to which the associated support member 39 or 43 is secured. The pivots formed by the fastener 63 are laterally aligned with the corresponding pivot points of the elongated members to which the cuffs are attached along the edge 59. The cuff members 57 are unsnapped and opened for applying the brace 23 to the extremity 3, and then are wrapped around and in front of the thigh and leg and snapped in place.

With the brace 23 in place, lateral blows to the leg 13 are partially absorbed by the muscles in the leg 13 with the remainder transmitted through the adjustable rigid posterior strut 25 to the elongated medial support member 43 which pulls the thigh 7 laterally with the leg and dissipates the transmitted energy into the muscles of the thigh. In response to a -lateral blow to the thigh 7, the force not absorbed by the thigh muscles is transmitted by the elongated support 43, around the knee joint 1 by the rigid posterior strut 25 and through the elongated support member 39 into the fleshy portion of the leg 13. The torsion force generated by rotation of the thigh with the foot planted is transmitted around the knee joint 1 by the rigid posterior strut 25, and through the elongated member 39 into the leg 13. The stiff cuff members 57 help to balance the rotational forces and to dissipate additional energy into the leg muscles. Anterior and posterior forces applied to the leg 13 or the thigh 7 are similarly transmitted around the knee joint 1 through the adjustable rigid posterior strut 25 with the assistance of the stiff cuff members 57.

Figure 3:
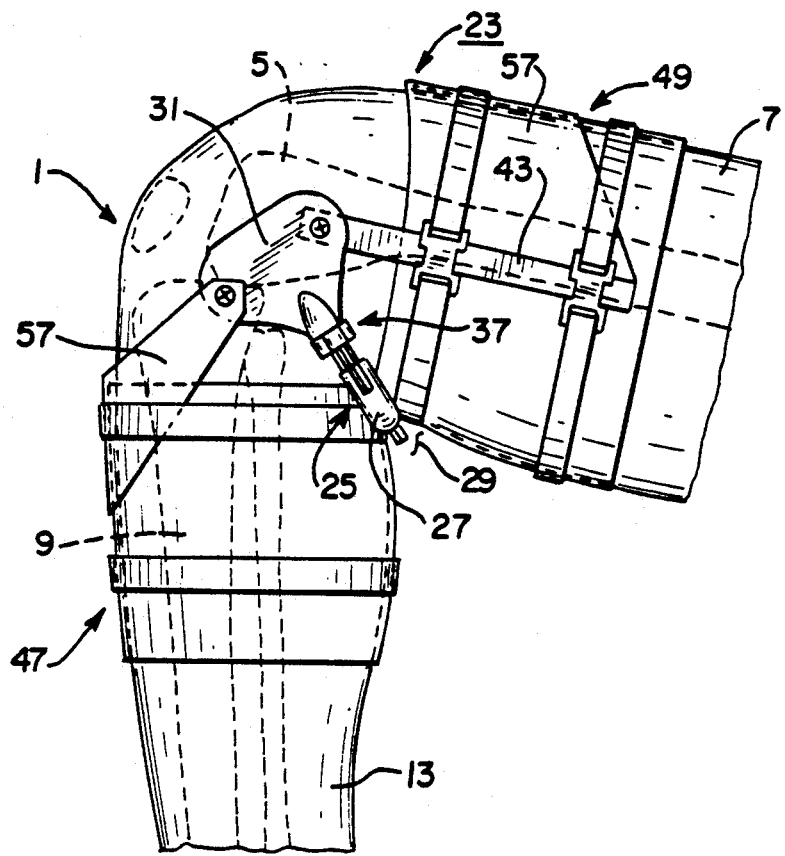
FIG. 3 is a side elevation view similar to FIG. 2 but showing the knee joint flexed.

Operation of the knee brace in accordance with the invention is illustrated by FIGS. 2 and 3. With the leg extended as shown in FIG. 2, the adjustable rigid posterior strut 25 extends substantially horizontally, rearward into the popliteal area 29 behind the knee joint 1. When the joint is flexed as shown in FIG. 3, the fleshy posterior portions of the leg (the calf) and thigh reposition the adjustable rigid posterior strut 25. This repositioning rotates the terminal portions 31 and 33 so that the pivot points at which the inferior and superior support members are attached are rotated to accommodate for the femoral rollback which is illustrated in FIG. 3. Thus, the knee brace in accordance with the invention is automatically and correctly positioned by the natural movement of the extremity 3 thereby eliminating the need for complex joint mechanisms which are sometimes ineffective because of slippage of the brace during flexion and extension.

FIG. 4 illustrates in detail the adjustable rigid posterior strut 25 of the invention. The arcuate member 27 has a longitudinal axis 65 and is composed of two halves 67 and 69, each of which is substantially a 90° sector of a circle. Confronting ends of the halves 67 and 69 have longitudinal bores 71. An elongated piece in the form of a pin 73 telescopes into the bores 71. Each of the halves 67 and 69 has a slit 75 extending the length of the bore 71. Confronting radial flanges 77 along either side of the slits 75 are drawn together by screws 79 to form clamps which secure the ends of the pin 73 in the bores 71 in a fixed position.

The free ends 81 and 83 of the halves 67 and 69, respectively, have longitudinal bores 85. Slots 87 through the walls of the arcuate members extend a substantial length along the bores 85. Confronting radial flanges 89 on either side of the slots 87 are drawn together by additional screws 91 to form clamps for securing the mounting members 35 and 37 to the arcuate member 27 as will be seen.

The mounting members 35 and 37 each have an elongated member in the form of a stem 93 which telescopes into the bore 85 in one of the halves 67 and 69 of the arcuate member 27 and is secured in a fixed position by the clamps formed by the flanges 89 and screws 91.

The terminal members 31 and 33 are secured to the mounting members 35 and 37, respectively, by adjustable attachments on the mounting members, preferably in the form of ball and socket connectors 95. As shown in FIG. 5, these connectors 95 include balls 97 on the ends of the mounting members 35 and 37. Bosses 99 on the rear edges of the terminal members 31 and 33 have rearwardly facing bores with spherical bottoms 101 which define the sockets for the balls 97. Lock nuts 103 which thread onto the outer surface of the bosses 99 clamp an annular ring 105 with a spherical inner surface against the ball 97 to lock the terminal members 31 and 33 in fixed positions relative to the mounting members 35 and 37.

As can be appreciated from FIG. 4, the adjustable rigid posterior strut 25 of the invention offers great flexibility in the adjustment of the brace 23. The adjustable connection between the two halves 67 and 69 of the arcuate member 27 of the posterior strut 25 allows adjustment of the lateral/medial distance between the terminal members 31 and 33 by loosening the screws 79, sliding the stem 73 in the bores 71, and then fixing the two halves in this position by tightening the screws 79. Adjustment of the position of the terminal members 31 and 33 relative to each other in the sagittal plane can be made by again loosening the screws 79 and rotating the halves 67 and 69 about the stem 73 to a desired position and then retightening the screws 79. Preferably, the stem 73, and the bores 71 are fluted as at 107 to aid in fixing the angular position of the two halves 67 and 69.

The strut 25 may be adjusted in the anterior/posterior direction through loosening of the screw 91 and sliding the stems 93 of the mounting members 35 and 37 inward or outward in the bores 85 in the ends 81 and 83 of the arcuate halves 67 and 69, and then retightening the screws 91. By loosening the screws 91 and rotating the mounting members 35 and 37 about the longitudinal axis 65 of the arcuate member 27 and then retightening the screws 91, the terminal members 31 and 33 can be rotated in the coronal plane to a desired fixed position relative to the arcuate member 27. Again, the stems 93 and bores 85 can be fluted as at 109 to lock the mounting members 35 and 37 in fixed positions relative to the arcuate members 27 with less torque required on the screws 91.

The ball and socket connectors 95 permit adjustment of the terminal members 31 and 33 in all three planes about the superior/inferior, medial/lateral and anterior/posterior axes relative to the mounting members 35 and 37.

Figure 6:
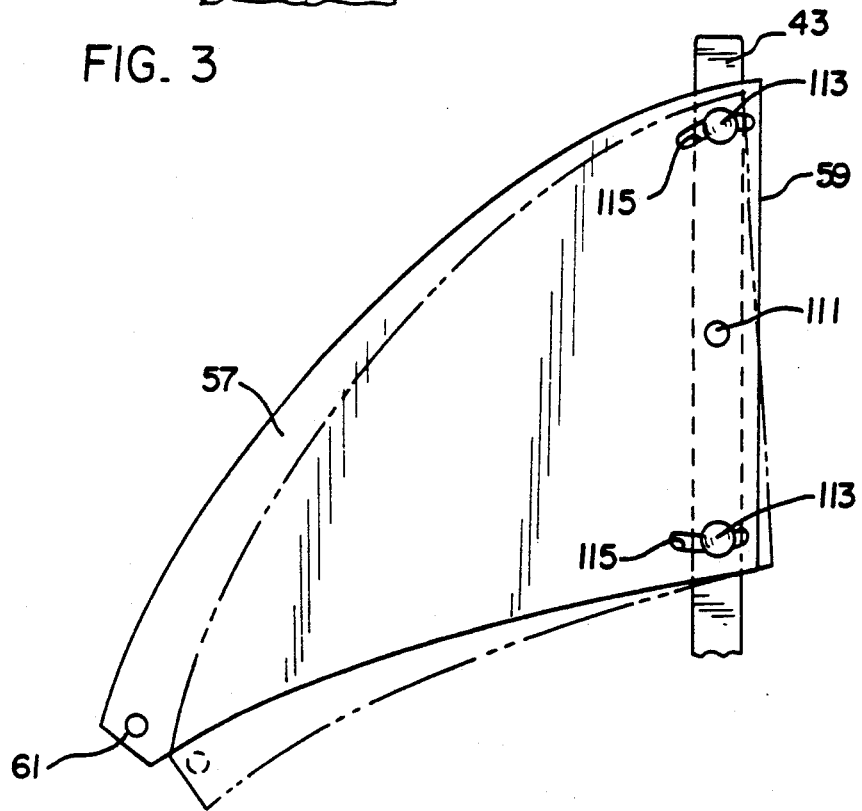
FIG. 6 is a fragmentary side view of a portion of the knee brace of the invention illustrating a mechanism for adjustment of the cuffs.

FIG. 6 illustrates a mechanism for adjustment of the anterior cuffs 57 which may be necessitated by adjustments, especially large adjustments, to the posterior strut 25. A pin 111 forms a fixed pivot for attaching the cuff member 57 to the elongated support member 43. Fasteners in the form of screws 113 extend through arcuate slot 115, which are generally transverse to the edge 59 of the cuff and spaced above and below the pivot pin 111. The screws 113, which are threaded into the elongated support member 43, are loosened to adjust the angular position of the cuff member 57 to align the vertex 61 with the fastener 63 on terminal member 31. The need for and the amount of this rotation is determined by the adjustment, if any, made to the posterior strut 25. The screws 113 are then tightened to clamp the cuff member 57 to the elongated support member 43 in the desired fixed angular position. A similar adjustment mechanism is provided for the cuff 57 secured to the other elongated support member 39.

For active (functional) use of the knee joint where maximum support is required, elongated support members pivoted to the strut 25 can be provided along both sides of the thigh and leg as described in U.S. patent application Ser. No. 07/662,879 which has been incorporated by reference into this application. Thus, a lateral superior elongated support member (not shown) may be pivoted to the terminal member 31, and secured to the thigh by an anchoring device 47. Similarly, a medial inferior elongated support member (not shown) can be pivoted to terminal member 33 and secured to the leg by an anchoring device 49. Additional anterior cuff members (not shown), attached to these additional elongated support members and criss-crossing in front of the thigh and leg can also be provided on the functional brace in accordance with the invention.

As the adjustable rigid posterior strut 25 serves as the central element to which the other elements of the brace 23 are connected, either directly or indirectly, the various adjustments made to the posterior strut 25 set the position of the other elements. The versatility of the adjustable knee brace in accordance with the invention allows an off the shelf brace to be used for patients with extremities of various sizes and shapes. Only a very few, perhaps two or three, sizes of brace need be stocked, as those stocked parts can be assembled and adjusted to cover a full range of sizes. Furthermore, the versatility of the adjustable brace allows it to be customized for the invariable deviations from the ideal knee joint and for a large range of deformities caused by disease or injury. Furthermore, the brace can be periodically adjusted during use to accommodate for changes such as the growth of a child, or a reduction in swelling.

The following table indicates in general terms exemplary problems or deformities, the conditions which typically give rise to this problem or deformity and the major adjustment to the posterior strut which may be used to compensate for this condition. It will be obvious that in many instances, the major adjustment will give rise to the need for additional adjustments at other connections to maintain the correct kinematics of the knee joint. For instance, if the two halves 67 and 69 of the arcuate member 27 are rotated about the pin 73, it may be necessary to rotate the mounting members 35 and 37 about the stem portions 93 and to adjust the ball and socket connections to maintain the terminal members 31 and 35 generally perpendicular to the axis of rotation of the knee joint.

TABLE 1

COMMON KNEE PROBLEMS AND RELATED CORRECTIONS USING POSTERIOR STRUT BRACE

| PROBLEM OR DEFORMITY | COMMON ASSOCIATED CONDITIONS | CORRECTION OF PROBLEM |
|---|---|---|
| Varus Deformity (bowed-kneed) | Osteoarthritis, Developmental | Tilt Posterior Strut in Coronal Plane (medial high) - rotate 67–69 about 73 |
| Valgus Deformity (knock-kneed) | Rheumatoid Arthritis, Osteoarthritis, Post-Traumatic | Tilt Posterior Strut in Coronal Plane (lateral high) - rotate 67 and 69 about 73 |
| Internal Rotation Deformity (pigeon-toed) | Developmental or Posti-traumatic Posteriolateral Ligamentous Laxity | Adjust Strut in Horizontal Plane Slide 93 in 85 (Elongated Laterally) |
| External Rotation Deformity (ballet dancer) | Developmental or Post-traumatic Posteromemdial Ligamentous Laxity | Adjust Strut in Horizontal Plane (extend on one side) - Slide 93 in 85 (Elongated Medially) |
| Flexion Contracture (can't straighten leg) | Osteoarthritis Post-operative, Rheumatoid Arthritis, Post-traumatic | Adjust Strut about Axis of Rotation. Rotate 31 or 33 relative to 27 |
| Extension Deformity | Developmental or Post-traumatic Ligamentous Laxity | Adjust Strut about Axis of Rotation. Rotate 31 or 33 relative to 27 |
| Growing Child | Normal Development of joints | Expand Strut. slide 67 and 69 on 73. Slide 93 out of 85 |
| Right/Left Differences | Various | Individually adjust L/R as required. |
| Swollen Knee | Post-traumatic or Post-operative Phlebitis | Expand Strut Slide 67 and 69 on 73 |
| Atrophied Knee | Post-injury Atrophy | Contract Strut Slide 67 and 69 on 73 |

It can be seen from the above that the invention provides great versatility to offset the axis of rotation of the brace, as well as individually adjust the lateral to medial distance and offset the vertical axis of action of the affected hinge point to compensate for individual knee characteristics, or to provide the surgeon/physiotherapist a means for adjusting for abnormal knees; for either improved brace fit; optimizing the brace function/action for individual patients; or compensating for, or controlling specific motions or actions.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An adjustable rigid posterior strut for a knee brace having elongated leg attachment members, said strut comprising:
   a rigid arcuate member having first and second ends and a longitudinal axis; first and second terminal members having pivot connections adapted for attachment to the elongated attachment member; and first and second mounting means rigidly fixing said first and second terminal members to said first and second ends respectively of said arcuate member in selected positions relative to said arcuate member.

2. The strut of claim 1 wherein said first and second mounting means comprise means adjustably fixing said first and second terminal members at selected fixed rotational positions about said longitudinal axis.

3. The strut of claim 1 wherein said first and second mounting means comprise means adjustably fixing said first and second terminal members at selected fixed axial positions along said longitudinal axis.

4. The strut of claim 1 wherein said first and second mounting means include means adjustably fixing said terminal members in selected fixed rotational positions about a lateral axis transverse to said longitudinal axis.

5. The strut of claim 1 wherein said first and second mounting means include means adjustably fixing said terminal members in selected fixed rotational positions about a vertical axis transverse to said longitudinal axis.

6. The strut of claim 1 wherein said first and second mounting means include mounting members having elongated members extendable axially with respect to said first and second ends of said arcuate member and rotatable about said longitudinal axis of said arcuate member, and first and second securing means fixedly securing said elongated members in selectable axial and rotational positions relative to said first and second ends respectively of said arcuate member.

7. The strut of claim 6 wherein said first and second elongated members telescope with said first and second ends respectively of said arcuate member, and said first and second securing means comprise clamps clamping said elongated members in selectable fixed axial and rotational positions relative to said first and second ends of said arcuate member.

8. The strut of claim 7 wherein said elongated members and said ends of said arcuate members are fluted.

9. The strut of claim 7 wherein said ends of said arcuate member have longitudinal bores in which said elongated members telescope, and wherein said ends have longitudinal slits extending along said bores and wherein said clamps comprise confronting flanges extending radially outward adjacent said slits and screw members drawing said flanges together to clamp said elongated members in said bores.

10. The strut of claim 9 wherein said elongated members and said bores are fluted.

11. The strut of claim 6 wherein said first and second mounting means further include first and second adjustable attachment means fixing said first and second terminal members in selectable positions to said first and second mounting members.

12. The strut of claim 11 wherein said first and second adjustable attachment means comprise ball and socket connections between said first and second terminal members respectively and one of said mounting members, and tightening means fixing said ball and socket connections with said first and second terminal members in selected positions relative to the mounting members.

13. The strut of claim 11 wherein arcuate member comprises first and second halves rotatable about said longitudinal axis to selectable angular positions with respect to one another, and connecting means fixedly connecting said first and second halves together at a selected angular position.

14. The strut of claim 6 wherein said arcuate member comprises first and second halves rotatable about said longitudinal axis to relative angular positions with respect to one another, and connecting means fixedly connecting said first and second halves together at a selected angular position.

15. The strut of claim 14 wherein said first and second halves are extendable axially along said longitudinal axis to selected axial positions relative to one another, and wherein said connecting means includes means fixedly connecting said first and second halves together at a selected axial position.

16. The strut of claim 15 wherein said connecting means includes an elongated piece which telescopes with and is rotatable about said longitudinal axis with respect to said first and second halves, and means clamping said elongated piece to said first and second halves with said first and second halves in said selected axial and angular positions with respect to one another.

17. The strut of claim 16 wherein said first and second halves have confronting longitudinal bores with longitudinal slits extending along said bores, wherein said elongated piece is a pin which telescopes and rotates in said bores, and wherein said clamping means comprises confronting radially, outwardly extending flanges along each side of said slits and screw members drawing said flanges together.

18. The strut of claim 6 wherein said arcuate member comprises first and second halves extendable axially along said longitudinal axis to selected axial positions relative to one another, and connecting means fixedly connecting said first and second halves together at a fixed axial position.

19. A brace for a knee joint joining thigh and leg limb members, said brace comprising:
a rigid posterior strut comprising a rigid arcuate member adapted to extend through a popliteal space behind the knee joint and having first and second ends and a longitudinal axis, first and second terminal members and first and second mounting means adjustably fixing said first and second terminal members to said first and second ends respectively of said arcuate member in selected axial and angular positions;
a first support member pivotally connected to said first terminal member and adapted to extend upward along a first side of the thigh;
a second support member pivotally connected to said second terminal member and adapted to extend downward along a second side of the leg opposite the first side of the thigh;
first support means adapted to secure said first support member to the thigh; and
second support means adapted to secure said second support member to the leg.

20. The brace of claim 19 including first and second generally triangular cuff members having a support edge and a vertex opposite said support edge, first attaching means firmly attaching the support edge of the first cuff member to the first support member with said first cuff member bowed anterior to the thigh and the vertex of the first cuff member pivotally attached to the second terminal member, and second attaching means firmly attaching the support edge of the second cuff member to the second support member with said second cuff member bowed anterior to the leg and the vertex of the second cuff member pivotally attached to the first terminal member.

21. The brace of claim 20 wherein said first and second attaching means comprise means firmly fixing the support edges of said first and second cuff members in selected axes of at least two positions relative to said first and second elongated members, respectively.

22. The brace of claim 20 wherein said first and second attaching means each comprise a pivot member pivotally securing a pivot point along the support edge of the first and second cuff members respectively to the support member, and fastening means spaced from said pivot member accommodating rotation of said cuff member about the pivot point to a selected angular position, and fixedly securing said support edge to said support member at said selected angular position.

23. The brace of claim 22 wherein said fastening means comprise a slot in said cuff member and a fastener extending through said slot and clamping said cuff member to said support member.

24. The brace of claim 22 wherein said fastening means comprise slots in said cuff member spaced in opposite directions along said support edge from said pivot member, and fasteners extending through each slot and clamping said cuff member to said support member.

25. The brace of claim 19 wherein said arcuate member has first and second halves rotatable about said longitudinal axis to a selected angular position with respect to one another, and extendable axially along the longitudinal axis to a selectable axial position with respect to one another, and connecting means fixedly connecting said first and second halves together at a selected angular and selected axial position.

26. The brace of claim 25 including first and second generally triangular cuff members having a support edge and a vertex opposite said support edge, first attaching means firmly attaching the support edge of the first cuff member to the first support member with said first cuff member bowed anterior to the thigh and the vertex of the first cuff member pivotally attached to the second terminal member, and second attaching means firmly attaching the support edge of the second cuff member to the second support member with said second cuff member bowed anterior to the leg and the vertex of the second cuff member pivotally attached to the first terminal member.

27. The brace of claim 26 wherein said first and second attaching means each comprise a pivot member pivotally securing a pivot point along the support edge of the first and second cuff members respectively to the support member, and fastening means spaced from said pivot member accommodating rotation of said cuff member about the pivot axis to a selected angular position, and fixedly securing said support edge to said support member at said selected angular position.

* * * * *

UNITED STATES PATENT AND TRADEMARK OFFICE
CERTIFICATE OF CORRECTION

PATENT NO. : 5,267,946
DATED : December 7, 1993
INVENTOR(S) : Samuel Singer et al.

It is certified that error appears in the above-indentified patent and that said Letters Patent is hereby corrected as shown below:

Claim 1, column 8, line 27, "member" should be --members--.

Signed and Sealed this

Twentieth Day of December, 1994

Attest:

BRUCE LEHMAN

Attesting Officer     Commissioner of Patents and Trademarks